(12) United States Patent
Elyasaf et al.

(10) Patent No.: US 7,518,718 B2
(45) Date of Patent: Apr. 14, 2009

(54) HIGH THROUGHPUT INSPECTION SYSTEM AND A METHOD FOR GENERATING TRANSMITTED AND/OR REFLECTED IMAGES

(75) Inventors: Emanuel Elyasaf, Rehovot (IL); Haim Feldman, Nof-Ayalon (IL); Simon Yalov, Ashdod (IL); Eitan Lahat, Yavne (IL)

(73) Assignee: Applied Materials, Israel, Ltd., Rehovot (IL)

( * ) Notice: Subject to any disclaimer, the term of this patent is extended or adjusted under 35 U.S.C. 154(b) by 0 days.

(21) Appl. No.: 11/425,101

(22) Filed: Jun. 19, 2006

(65) Prior Publication Data

US 2006/0221331 A1  Oct. 5, 2006

Related U.S. Application Data

(63) Continuation of application No. 11/127,914, filed on May 11, 2005, now Pat. No. 7,187,439, which is a continuation of application No. 10/215,972, filed on Aug. 8, 2002, now Pat. No. 6,930,770.

(51) Int. Cl.
   G01N 21/88   (2006.01)
(52) U.S. Cl. .................................. 356/237.5; 356/239.8
(58) Field of Classification Search ... 356/237.1–237.5, 356/239.1–239.2, 239.7, 239.8
   See application file for complete search history.

(56) References Cited

U.S. PATENT DOCUMENTS

| | | | |
|---|---|---|---|
| 5,191,393 A | 3/1993 | Hignette et al. | |
| 5,386,112 A | 1/1995 | Dixon | |
| 5,572,598 A | 11/1996 | Wihl | |
| 5,892,579 A | 4/1999 | Elyasef et al. | |
| 6,175,645 B1 | 1/2001 | Elyasef et al. | |
| 6,603,543 B1* | 8/2003 | La Fontaine | 356/237.5 |
| 6,930,770 B2* | 8/2005 | Elyasef et al. | 356/237.1 |
| 7,187,439 B2* | 3/2007 | Elyasef et al. | 356/237.5 |
| 2002/0012376 A1 | 1/2002 | Das et al. | |

FOREIGN PATENT DOCUMENTS

| | | |
|---|---|---|
| EP | 0557227 A2 | 8/1993 |
| EP | 0819933 A2 | 1/1998 |

OTHER PUBLICATIONS

Masaki Toshimichi, Patent Abstracts of Japan, Device and Method for Processing Image and Inspecting Method, Omron Corp, Pub. No. 2001101416, U.S. Appl. No. 11/278,865, Publication date Apr. 13, 2001.

* cited by examiner

*Primary Examiner*—Hoa Q Pham
(74) *Attorney, Agent, or Firm*—Tarek N. Fahmi

(57) ABSTRACT

Inspection system and method for high-throughput inspection, the system and method is capable to generate and sense transmitted and/or reflected short duration beams. According to one embodiment of the invention the transmitted and reflected short duration beams are generated and sensed simultaneously thus provide a reflected image and a transmitted image simultaneously. The reflected and transmitted short duration radiation beams are manipulated either in the frequency domain or are distinctly polarized such that they are directed to the appropriate area sensors. According to another aspect of the invention the system changes the manipulation of a short duration beam of radiation to selectively direct the short duration beam to distinct area sensors.

12 Claims, 8 Drawing Sheets

RECTANGULAR PORTION 9(1)

REFLECTED IMAGE 94

TRANSMITTED IMAGE 92

HIGH THROUGHPUT INSPECTION SYSTEM AND A METHOD FOR GENERATING TRANSMITTED AND/OR REFLECTED IMAGES

RELATED APPLICATIONS

The present application is a Continuation of and incorporates by reference-U.S. patent application Ser. No. 11/127,914 filed May 11, 2005, now U.S. Pat. No. 7,187,439, which is a Continuation of and incorporates by reference U.S. patent application Ser. No. 10/215,972, filed Aug. 8, 2002, now U.S. Pat. No. 6,930,770.

FIELD OF THE INVENTION

The present invention relates to a system and method for high throughput inspection of an object using short duration reflective and transmitted radiation beams, such as but not limited to radiation beams.

BACKGROUND OF THE INVENTION

Systems and methods of inspecting an article to determine the condition of the article, such as a mask (also referred to as reticle or photomask) are known in the art. Optical inspection systems and methods involve directing a radiation beam onto an inspected object and detecting the radiation reflected from the system or the radiation transmitted through the object.

The size of transistors is constantly being reduced and there is a need to inspect masks (also known as reticles) with higher resolution. In spite of the required higher resolution there is a need to perform optical inspections in a time efficient manner. There is therefore a need to provide a system and method for inspection that is characterized by both high throughput and high resolution.

SUMMARY OF THE INVENTION

The invention provides a system and method for high throughput optical inspection. The method includes the steps of: (i) Reflecting a first beam of radiation from one face of an area of the object to produce a short duration reflected beam and simultaneously transmitting a second beam of radiation through the area of the object including the first face and a second face to provide a short duration transmitted beam; (II) Sensing the short duration reflected beam and the short duration transmitted beam and in response generating output signals reflecting a condition of the area of the object; (III) Periodically repeating steps (I) and (II) until a predefined portion of the object is irradiated; and (IV) Processing the output signals to provide an indication of the condition of the predefined portion of the object.

The invention provides an optical inspection system that has reflected and transmitted radiation paths, that enable short duration reflected and transmitted radiation beams to be simultaneously generated and directed towards area sensors to simultaneously provide a transmitted and reflected images of the inspected objects. Accordingly, the system and method enable simple comparison between transmitted and reflected images of an area (and accordingly simplify the registration process and even eliminate the need for performing registration between transmitted and reflected images) as both a transmitted image and a reflected image of an area are taken simultaneously.

The invention provides an optical inspection system of high throughput by manipulating either reflected or transmitted beams so that images are formed at alternating area detectors.

BRIEF DESCRIPTION OF THE DRAWINGS

Further features and advantages of the invention will be apparent from the description below. The invention is herein described, by way of example only, with reference to the accompanying drawings, wherein.

DETAILED DESCRIPTION OF THE EMBODIMENTS

As indicated earlier, the method and apparatus of the present invention are particularly useful for optically inspecting photomasks in order to detect defects in reflecting and/or transmissive areas of the photomask. It is noted that some photomasks have clear areas and opaque areas alone, while other photomasks may include areas that are characterized by reflection and/or transmission levels between full reflection/transmission and zero reflection/transmission. For example, a halftone area permits only about % of light to pass through it. For simplicity of explanation alone it is assumed that the photomask has clear and opaque areas.

Electromagnetic radiation beams may be characterized by their polarization. The electric field of a linearly polarized optical wave lies only in a single plane. The electric fields of a circularly polarized optical wave lie in two orthogonal planes and are phased shifted by a quarter wavelength (or an odd amount of quarter wavelengths) of the optical wave. Polarizing beam splitters divide an optical wave that has electric fields in two orthogonal planes into two orthogonally polarized optical waves. Phase retardation involves making an optical path length for one out of two orthogonal linear polarizations different than each other. Quarter wave retarders convert linearly polarized optical waves into circularly polarized optical waves and vice versa. Variable retarders are able to change their retardance and accordingly are able to change the relative phase shift between the electrical fields in two orthogonal planes, thus introducing a phase shift. Variable wave retarders may change their retardance between zero and a portion of a wavelength. Variable wave retarders are characterized by the maximal amount of phase shift they introduce. For example a half wavelength variable retarder is able to change its retardance between zero and a half wavelength. Phase retarders such as but not limited to quarter wavelength retarders and polarizing beam splitters are known in the art.

Figure 1A:
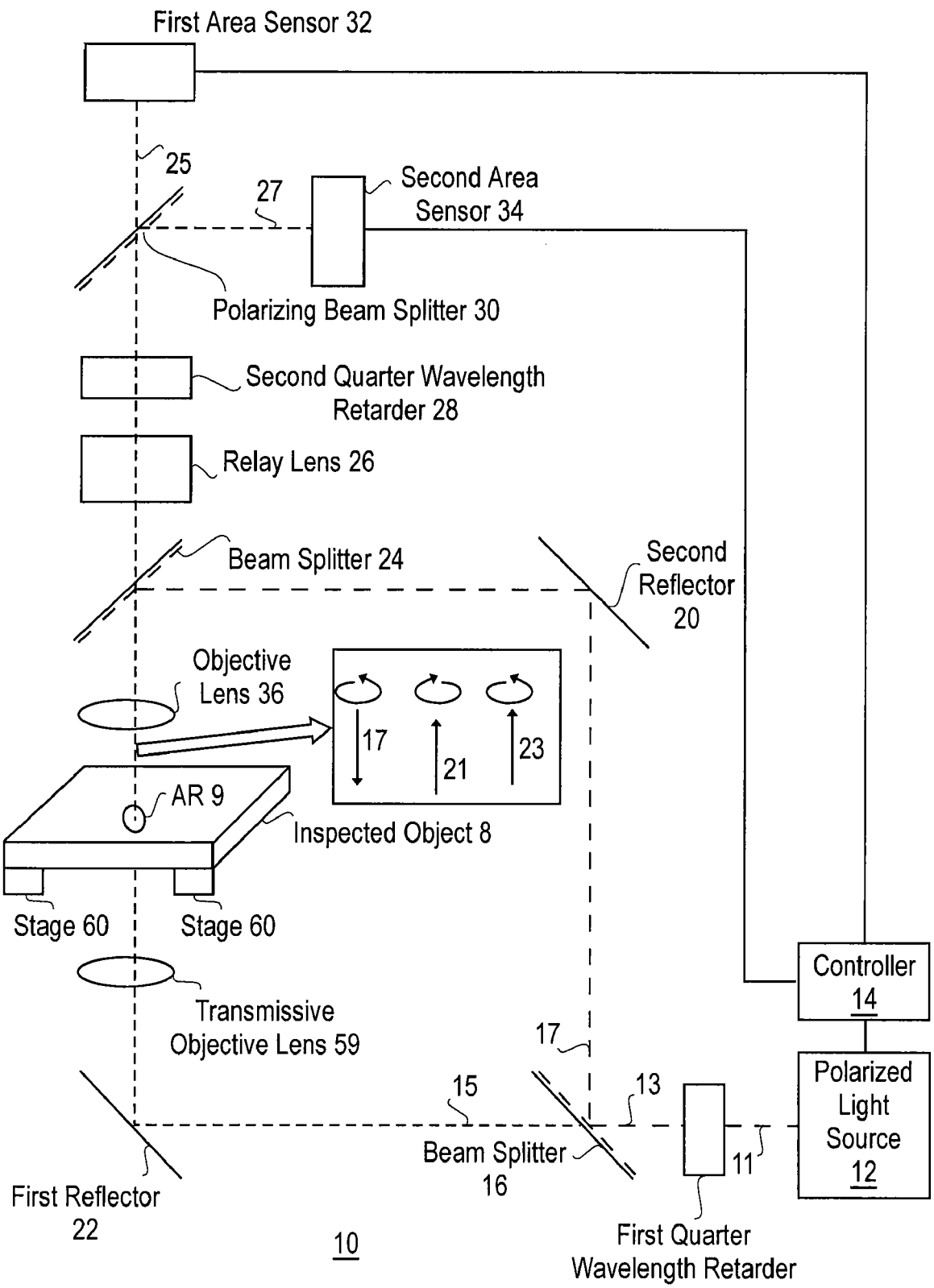
FIGS. 1a-1c are schematic diagrams illustrating optical inspection systems constructed in accordance with the present invention.

FIG. 1a illustrates an optical inspection system 10, in accordance with an embodiment of the invention. System 10 includes a radiation source. Preferably the radiation has a wavelength of about 193 nm. It is further noted that the radiation source is located below a plane in which the inspected object is located, but this is not necessarily so.

System 10 includes a linearly polarized radiation source 12, controller 14, first quarter wave retarder 11, beam splitter 16, first reflector 22, stage 60, objective lens 36, beam splitter 24, relay lens 26, second quarter wavelength retarder 28, polarized beam splitter 30, optics such as transmissive objective lens 59, first area sensor 32 and second area sensor 34.

It is noted that polarized radiation source 12, first quarter wave retarder 11, beam splitter 16, first reflector 22, objective lens 36, transmissive objective lens 59, beam splitter 24, relay lens 26, second quarter wavelength retarder 28 and polarized beam splitter 30 define an illumination system having reflected and transmitted paths.

Polarized radiation source, such a laser 12 is operable to generate short duration radiation beams of a linear polarization, such as a horizontal polarization (e.g.—the electrical fields of the radiation beam lie in the XZ plane, while the short duration radiation beam propagates along the X axis.). Controller 14, coupled to laser 12, is operable to control the generation of the short duration radiation beams in accordance with an irradiation pattern (also termed illumination pattern). Conveniently, the irradiation pattern includes a series of time spaced pulses. The irradiation pattern is responsive to various parameters such as the radiation source parameters (usually maximal duty cycle), and required throughput. Those of skill in the art will appreciate that as the wavelength of radiation pulses continues to decrease the complexity and cost of high duty cycle lasers substantially increases.

Laser 12 is followed by a quarter wave retarder 11 that produces a circularly polarized (assuming Right Hand Circularly (i.e.—RHC) polarized) short duration radiation beam 13. The RHC polarized short duration radiation beam 13 is split by beam splitter 16 to a first and second short duration radiation beams 15 and 17 respectively. The first short duration radiation beam 15 is directed towards first reflector 22 to be reflected towards the lower face of the inspected object 8, and especially towards an lower face of an area AR 9 of the inspected object, whereas AR 9 is defined by the cross section of the first short duration radiation beam 15. It is noted that the intensities of the first and second short duration radiation beams 15 and 17 may be equal but this is not necessarily so.

The first short duration radiation beam 15 is partially transmitted through clear portions of area AR 9 to produce short duration transmitted beam 21. The second short duration radiation beam 17 is partially reflected from opaque portions of area AR 9 to produce a short duration reflected beam 23. Short duration reflected beam is RHC polarized, while short duration transmitted beam 21 is LHC polarized, as the polarization of the former is reversed as result of the reflection.

Figure 3:
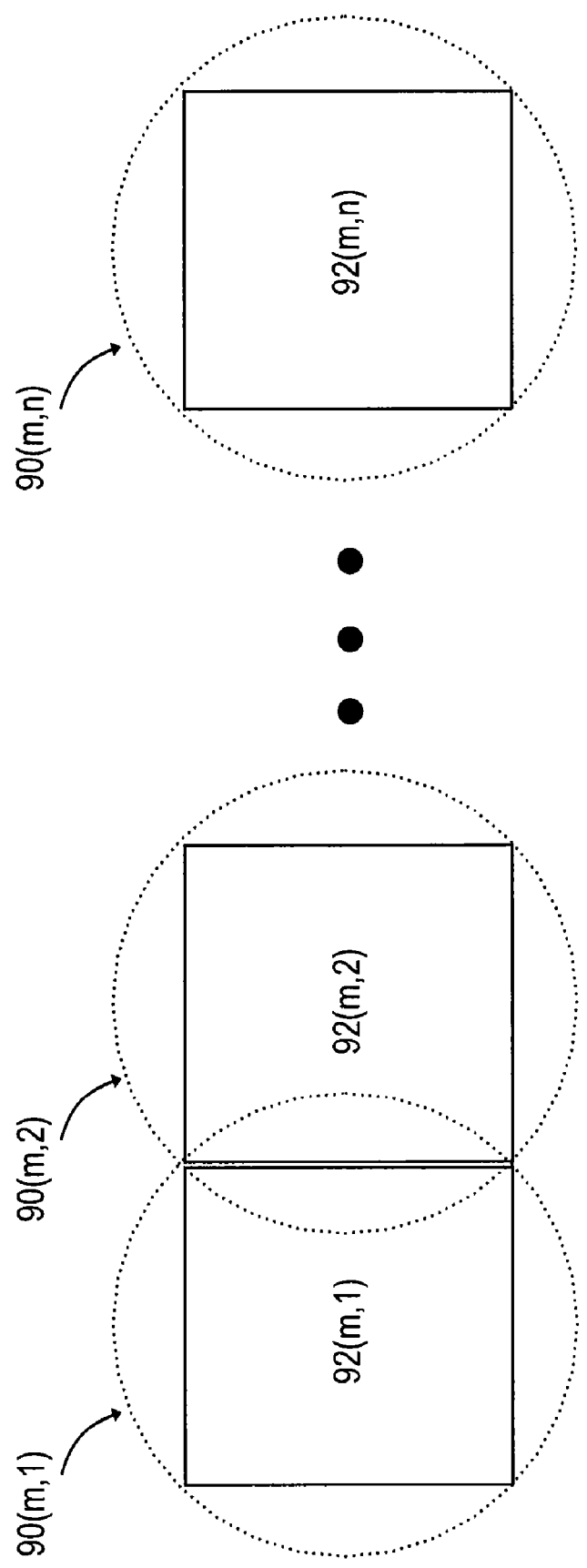
FIG. 3 illustrates a scanning scheme in accordance with an embodiment of the invention.

Short duration transmitted beam 21 and short duration reflected beam 23 are collected by objective lens 36 that is positioned above the upper face of the inspected object 8, whereas AR 9 is located at a focal plane of objective lens 36. Short duration transmitted beam 21 and short duration reflected beam 23 pass through beam splitter 24 to propagate through relay lens 26. Relay lens 26 is operative to match the size of the image of AR 9 or, as illustrated by FIG. 3, the size of an image of a rectangular portion of area AR 9 to the sensing surfaces of area sensors 34 and 32. It is noted that the sensing surface of area sensors 32 and 34 are rectangular, while the cross section of the short duration reflected and transmitted radiation beams is circular, but this is not necessarily so, as the short duration reflected and transmitted radiation beam may be shaped to fit the shape of the sensing area, and vice verse.

Figure 2A:
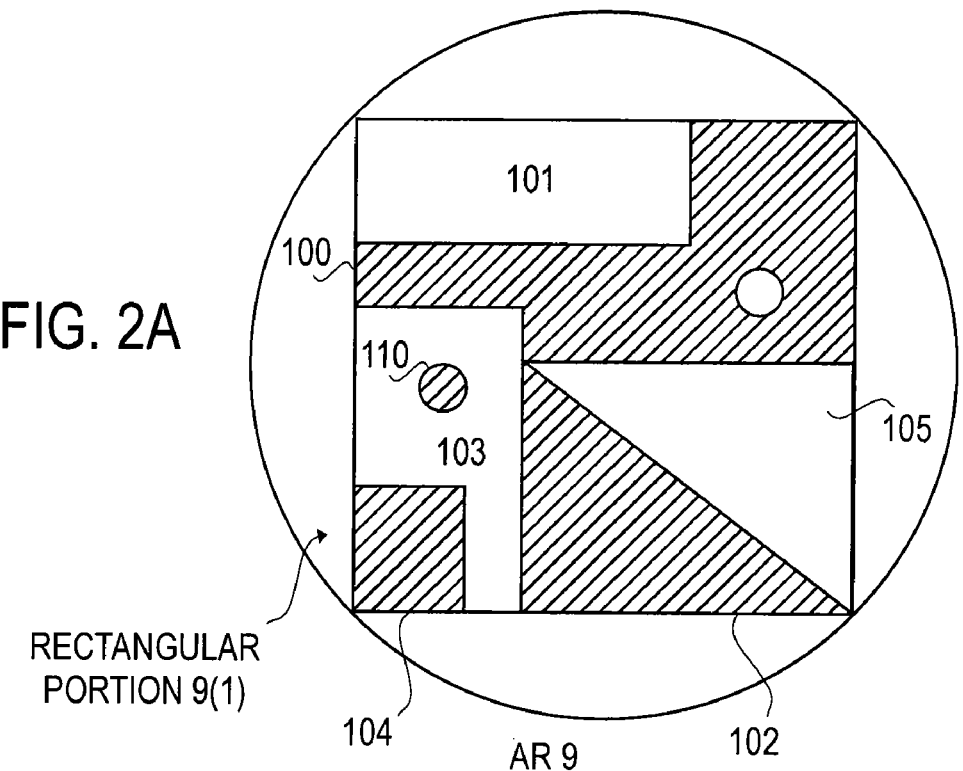
FIGS. 2a-2c illustrate transmitted and reflected images of an area, in accordance with an embodiment of the invention.
Figure 2B:
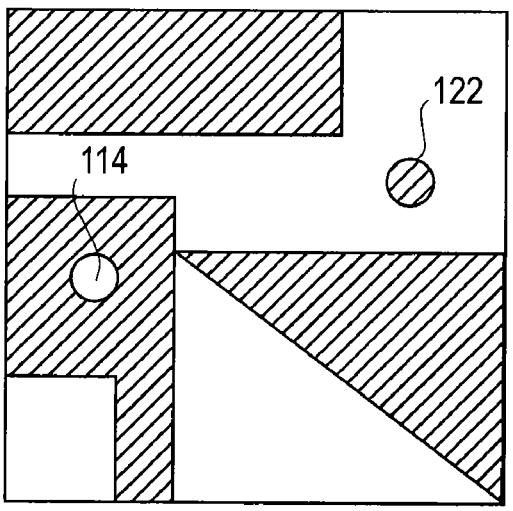
Figure 2C:
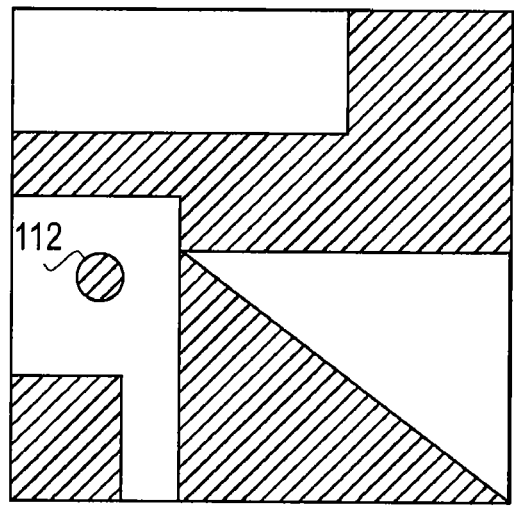

After propagating through relay lens 26 the short duration transmitted beam 21 and short duration reflected beam 23 pass though second quarter wavelength retarder 28 that converts the LHC polarized short duration transmitted beam 21 and the RHC polarized short duration short duration reflected beam 23 to a linearly polarized radiation beam in the X direction (also referred to as p-polarized radiation beam) 25 and to a linearly polarized radiation beam in the Z direction (also referred to as s-polarized beam) 27. Both beams 25 and 27 are directed towards polarizing beam splitter 30 that directs the p-polarized radiation beam 25 towards a first area sensor 32 and directs the s-polarized radiation beam 27 towards a second area sensor 34. Thus, the first area sensor 32 receives a transmitted image of AR 9 (or of a portion of AR 9) while the second area sensor 34 receives a reflected image of AR 9 (or of a portion of AR 9), as illustrated in FIG. 2a-2c.

Figure 1B:
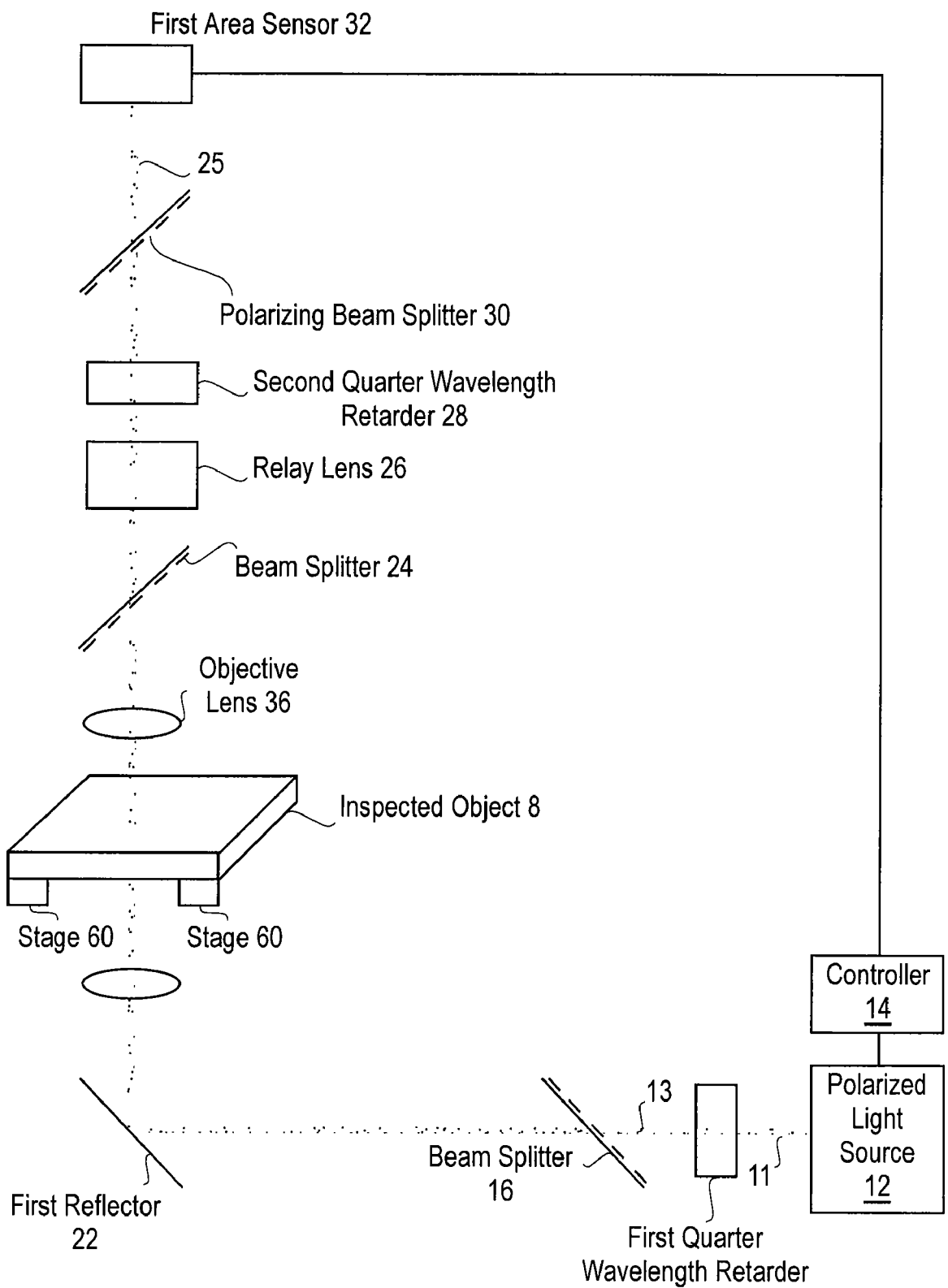
Figure 1C:
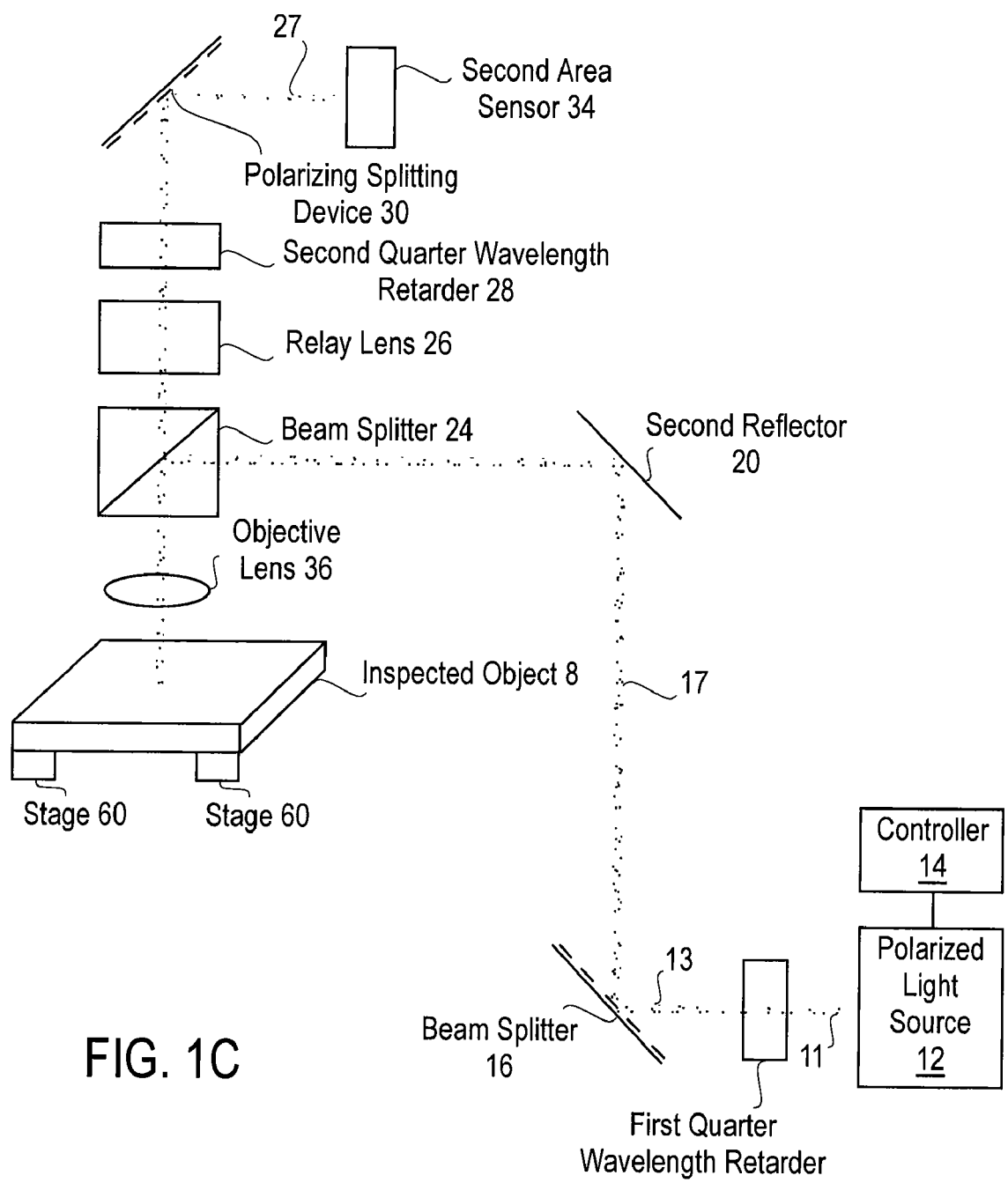

FIG. 1a illustrates the propagation of both reflected and transmitted radiation beams that enable the generation of a reflected and a transmitted image of an area respectfully, whereas FIG. 1b illustrates the propagation of the short duration transmitted radiation beam alone and FIG. 1c illustrates the propagation of the short duration reflected radiation beam alone.

Preferably, first area sensor 32 and second area sensor 34 are back illumination CCD area sensors having an array of 1024×1024 sensing elements. The 1024×1024 array is partitioned in multiple segments, for enabling parallel reading of the multiple segments and enhancing the system throughput. CCD area sensors are available from several vendors, such as Dalsa, Sarnoff or Fairchild. Typical data readout rates of a single CCD area sensor range between ten mega pixels per second to several hundreds mega pixels per second. Alternative configurations of detection elements and segments may also be used, as will be apparent to those skilled in the art.

The first area sensor 32 and second area sensor 34 are operable to (a) sense the short duration transmitted beam and the short duration reflected beam, respectively, and, in response, to (b) generate output signals reflecting a condition of the irradiated area of the object. The output signals reflect the charge of each sensing element, the charge being responsive to the intensity of radiation that is incident on the sensing element. In other words, the output signals of first area sensor 32 represent a transmitted image received by the first area sensor 32, while the output signals of second area sensor 34 represent a reflected image received by the second area sensor 34.

Those of skill in the art will appreciate that other polarization schemes such as ellipsoid polarization and linear polarization may be utilized for separating the short duration reflected beam and short duration transmitted beam.

FIGS. 2a-2c illustrate an exemplary area AR 9 and especially a rectangular portion 9(1) of AR 9. Portion 9(1) has opaque portions 100, 102, 104 and 106, clear portions 101, 103 and 105 and foreign particle 110 and 120. The clear and opaque portions are in the form of bright and dark areas in the transmitted image 92 of FIG. 2b while being in the form of dark and bright areas in the reflected image 94 of FIG. 2c. Foreign particle 110 that is located above clear portion 103 can be seen as a radiation falloff (112) in the transmitted image 92 and as a spot (114) that has a different brightness than its surroundings in the reflected image 94. Foreign particle 120 that is located above opaque portion 104 can be seen as spot 122 in the reflected image 94.I Referring back to FIGS. 1a-1c, controller 16 is operable to initiate the reflection, transmission and sensing of short duration radiation beams until a predefined portion of the object is radiated and is further operable to process the output signals to provide an indication of the condition of the predefined portion of the object. Various signal processing schemes are known in the art, such as a comparison between the reflected image and the transmitted image. As both images are acquired simultaneously, there is no need to perform a registration between these images, thus simplifying the processing stage and improving the accuracy of the image processing.

Stage 60 is operable to hold the inspected object and translate it such that a predefined portion of the inspected object is illuminated during a series of reflection, transmission and detections iterations. The illuminated areas and especially the portions that are later imaged on the area sensors overlap, thus reducing the sensitivity of system 10 to mechanical vibrations and for preventing gaps in the coverage of the inspected object. Usually, stage 60 translates the inspected object such that a predefined portion of the inspected object is irradiated. Preferably, the inspected object is raster scanned, but other scanning schemes may also be implemented.

FIG. 3 illustrates a scanning scheme in which the inspected object is translated along a scan (X) axis and a row of partially overlapping circular areas 90($m$, 1)-90($m,n$) is illuminated during a series of time spaced short duration radiation pulses. It is noted that a rectangular portion (denoted 92($m$, 1)-90($m,n$)) of each of said circular areas 90($m$, 1)-90($m,n$) is imaged on the sensing surfaces of first area sensor 32 and second area sensor 34, but this is not necessarily so. For example, the radiation beams may be shaped as to illuminate a rectangular area, or the first area sensor and second area sensor may have a circular shaped sensing surface.

Figure 4:
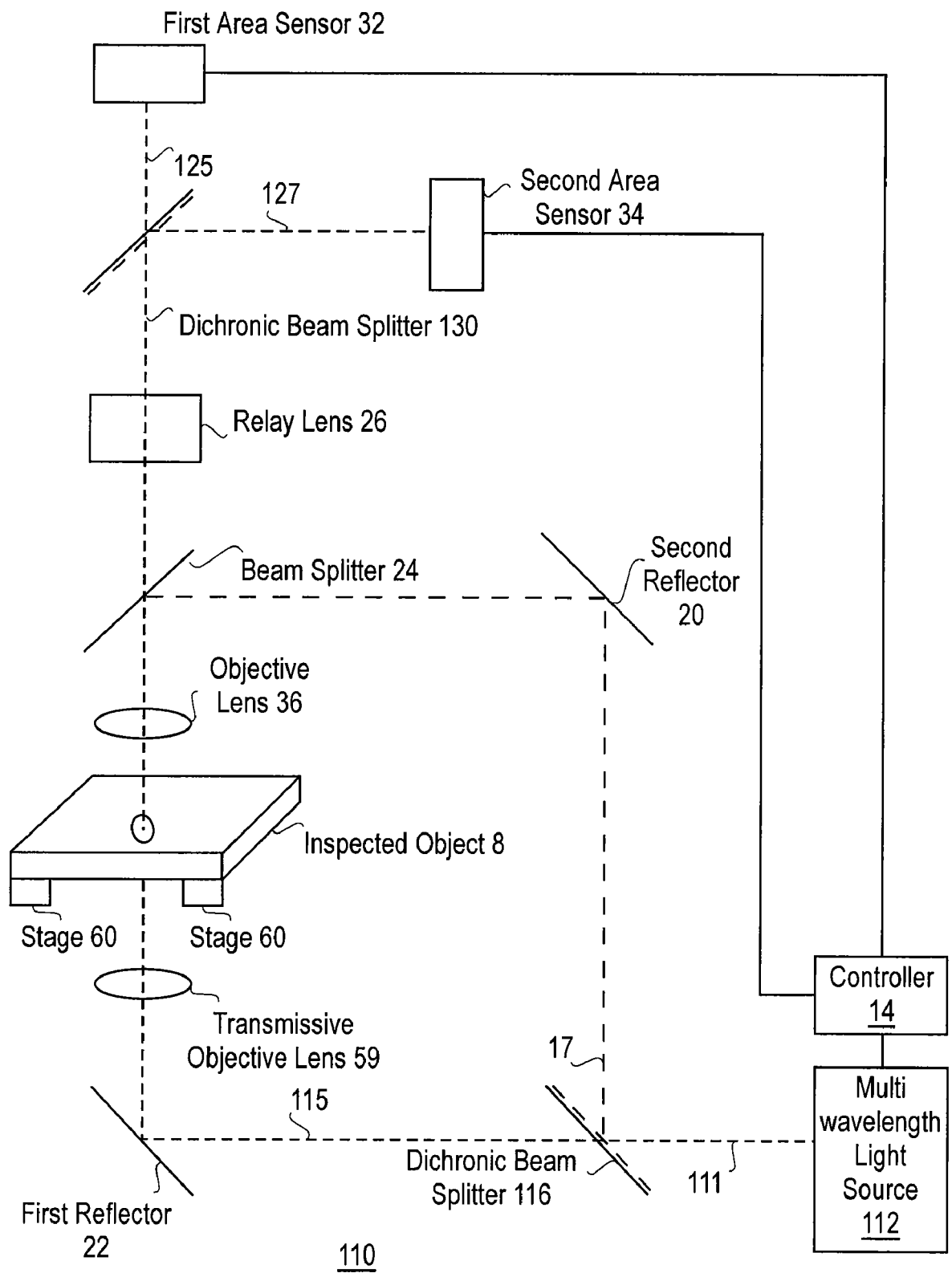
FIGS. 4-5 are schematic diagrams of optical inspection systems in accordance with other embodiments of the present invention.

FIG. 4 illustrates an optical inspection system 10, in accordance with another embodiment of the invention. System 110 differs from system 10 in that the differentiation between the transmitted and reflected beams that generate the transmitted and reflected images is based upon wavelength but not upon polarization. In other words, the short duration reflected radiation beam differs from the short duration transmitted radiation beam by wavelength. It is noted that the generation of short duration radiation beams of distinct wavelength may be implemented by using distinct radiation sources, but when dealing with ultra short radiation pulses (such as picosecond to nanosecond radiation pulses) the synchronization between distinct radiation sources is very complex, thus using a single radiation source for generating the short duration radiation pulses is more feasible and much more accurate. Accordingly, a single radiation source generates multi-wavelength short duration radiation pulses that are later filtered to split multiple short duration radiation beams of distinct wavelength.

As system 110 is based upon wavelength separation, the polarizing and polarization based elements of system 10 (such as first quarter wave retarder 18, second quarter wavelength retarder 28, beam splitter 16 and polarized beam splitter 30) are replaced by dichronic beam splitters 116 and 130.

As system 110 is based upon wavelength separation, the polarizing and polarization based elements of system 10 (such as first quarter wave retarder 18, second quarter wavelength retarder 28, polarized beam splitter 30) are replaced by dichronic beam splitter 116 and 130.

System 110 includes polychromatic radiation source 112 that generates multi-wavelength short duration radiation beams 111, that are directed towards dichroic beam splitter 116, that splits said beam to provide a first wavelength short duration beam 115 that is directed towards first reflector 22, and to provide a second wavelength short duration beam 117 that is directed towards second reflector 20.

First wavelength short duration beam 115 is reflected from first reflector 22, passes through optics, such as transmissive objective lens 159, and passes through clear portions of illuminated area AR 9, is collected by objective lens 36, passes through relay lens 26 and is split by diachronic beam splitter 130 to two portions 125 and 135. First portion 125 passes through first spectral filter 116 and arrives to first area sensor 32 and forms a transmitted image of AR 9, while a second portion 135 is blocked by second spectral filter 114 thus does not arrive to second area sensor 34.

Second wavelength short duration beam 117 is reflected from second reflector 20, is reflected from opaque portions of illuminated area AR 9, is collected by objective lens 36, passes through relay lens 26 and is split by beam splitter 130 to two portions 127 and 137. First portion 127 is blocked by first spectral filter 112 thus does not arrive to first area sensor 32, while second portion 137 passes through second spectral filter 114 and arrives to second area sensor 34 and forms a reflected image of AR9.I First and second array sensors 32 and 34 simultaneously send to controller 14 electrical signals representative of a transmitted and reflected images of area AR9, respectively. Controller 14 processes the images to determine the condition of area AR9.

It is noted that polychromatic radiation source 112, diachronic beam splitters 116 and 130, first reflector 22, relay lens 26 and transmissive objective lens 159 define an illumination system that has a reflective and transmitted radiation paths.

Figure 5:
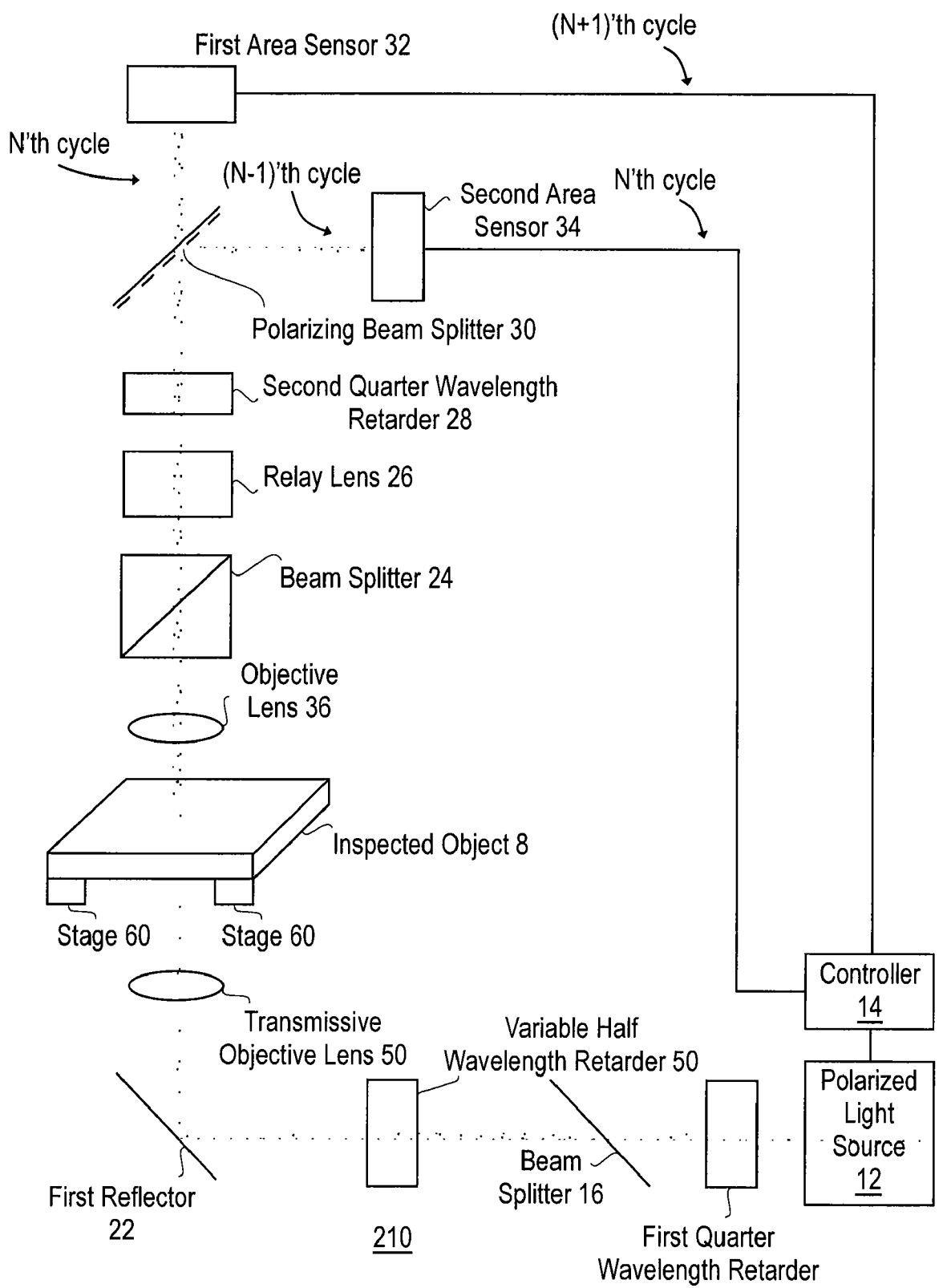

FIG. 5 illustrates an optical inspection system 210, in accordance to a further
embodiment of the invention. System 210 generates only transmitted images but is characterized by a very high throughput.

It is known in the art that area detectors that include multiple sensing elements, such as area CCD cameras, are limited by their data readout rate. It is known that although an image is formed in parallel at the sensing elements of a CCD camera, the sensing elements are read in a serial manner. In some CCD cameras the multiple sensing elements are partitioned to segments, each segment including sensing elements that are coupled to each other in a serial manner. Each segment may be read in parallel to the other segment, thus increasing the overall readout rate of the CCD camera, but this may not provide the required readout rate. Another method for multiplying the data readout rate involves buffering the sensing element readout within the CCD camera, but this solution is very costly.

System 210 enables an increase in the throughput of an inspection system by utilizing two CCD cameras while alternating the polarization of the radiation beam and accordingly alternating the area sensing element that generates the image.

System 210 may have a transmitted radiation path alone that includes first quarter wavelength retarder 16, a fast variable half wavelength retarder 50, first reflector 22, stage 60, objective lens 36, relay lens 26, second quarter wavelength retarder 28, polarized beam splitter 30, first area sensor 32 and second area sensor 34. First quarter wavelength retarder 16, fast variable half wavelength retarder 50, first reflector 22, stage 60, objective lens 36, relay lens 26, second quarter wavelength retarder 28 and polarized beam splitter 30 define a illumination system that has a transmitted radiation path.

Fast variable half wavelength retarder 50 is able to change the polarization of the transmitted radiation beam from RHC polarization and LHC polarization, in response to control signals from controller 14. The change rates may be adjusted/ selected to fit the readout period out of each area sensor. It usually ranges between several hundred changes per second, but this is not necessarily so.

When the variable half wavelength retarder 50 does not change the polarization of the radiation beam the transmitted radiation beam arrives to the first area sensor 32, while when the variable half wavelength retarder 50 introduces a phase shift of half a wavelength, the transmitted radiation beam arrives to the second area sensor 34.

The timing of beam transmission and electrical transmission to processor 14 is illustrated by "N'th cycle", "(N−1)'th cycle" and "(N+1)'th cycle" reflecting that an image is directed towards second area sensor 34 during a (N−1)'th cycle, that an image is directed towards first area sensor 32 and that output signals (that reflect the image that is generated during the (N−1)'th cycle) are provided from second area sensor 34 to controller 14 during a N'th cycle and that during the (N+1)'th cycle output signals (that reflect the image that is generated during the N'th cycle) are provided from first area sensor 32 to controller 14.

Those of skill in the art will appreciate that system 210 may include a reflective path alone, whereas the reflected path includes a half wavelength retarder, beam directing elements such as reflectors and beam splitters.

If is further noted that the elements of systems 10 and 210 may be combined, [0050] to allow the generation of reflected and transmitted images, or to allow the generation of transmitted images alone or reflected images alone (when the half wavelength retarder is located at a reflected radiation path).

Figure 6:
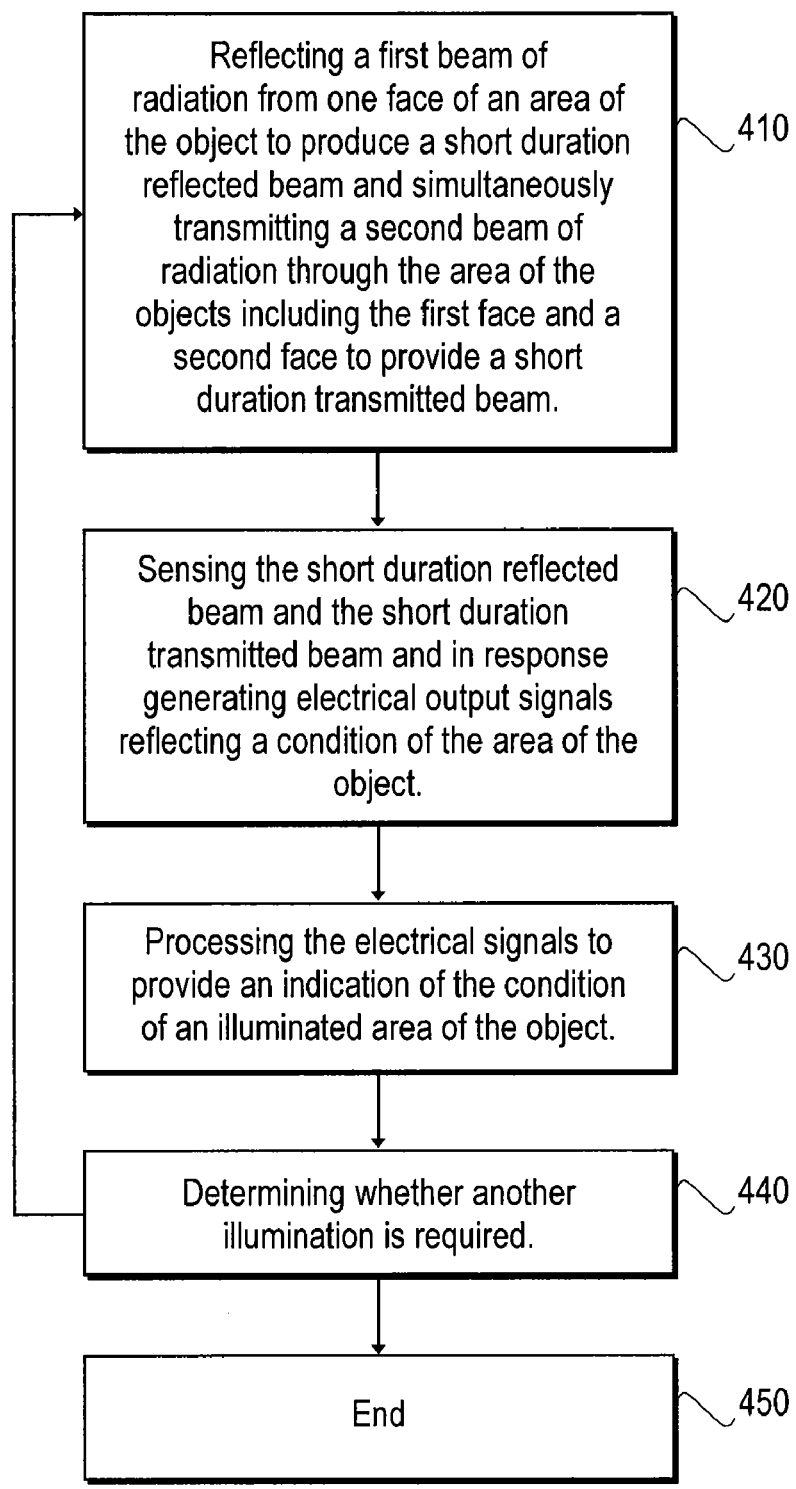
FIG. 6 is a flow chart illustrating a method for inspecting an object, according to embodiments of the invention.

Referring to FIG. 6 illustrating a method 400 for inspecting an object.

Method 400 starts at step 410 of reflecting a first beam of radiation from one face of an area of the object to produce a short duration reflected beam and simultaneously transmitting a second beam of radiation through the area of the object including the first face and a second face to provide a short duration transmitted beam.

Step 410 is followed by step 420 of sensing the short duration reflected beam and the short duration transmitted beam and in response generating output signals reflecting a condition of the irradiated area.

Step 420 is followed by step 430 of processing the electrical signals to provide an indication of the condition of an illuminated area of the object. Step 430 is followed by step 440 of determining whether another illumination is required (e.g.—if the predefined portion was already illuminated) and if so—step 440 is followed by step 410 such that steps 410—440 are periodically repeated until the predefined portion of the object is radiated. Else, step 440 is followed by "END" step 450.

It is noted that FIG. 6 illustrates a method in which the processing is done during the illumination and determination steps, but this is not necessarily so as the electrical signals may be stored and later on processed.

It will thus be appreciated that the preferred embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A method of optically inspecting an object for indicating a condition of the object, comprising the steps of:
    sending a beam of radiation;
    modifying the beam of radiation and reflecting the modified beam of radiation from a face of an area of the object so that the reflected beam alternately arrives at a first area sensor and a second area sensor;
    sensing the reflected beam that arrives at the first area sensor by the first area sensor and generating first output signals in response;
    sensing the reflected beam that arrives at the second area sensor by the second area sensor and generating second output signals in response;
    repeating a cycle of modifying, reflecting and sensing until a predefined portion of the object is radiated, wherein during each cycle, at least one of the first and second output signals are available to be processed; and
    processing the first and second output signals to provide an indication of the condition of the predefined portion of the object.

2. The method of claim 1 wherein the modifying of the beam of radiation comprises changing a frequency of the beam of radiation.

3. The method of claim 1 wherein the modifying of the beam of radiation comprises polarizing the beam of radiation.

4. A method of optically inspecting an object for indicating a condition of the object, comprising the steps of:
    sending a beam of radiation;
    modifying the beam of radiation and transmitting the modified beam of radiation from a face of an area of the object so that the transmitted beam alternately arrives at a first area sensor and a second area sensor;
    sensing the transmitted beam that arrives at the first area sensor by the first area sensor and generating first output signals in response;
    sensing the transmitted beam that arrives at the second area sensor by the second area sensor and generating second output signals in response;
    repeating a cycle of modifying, transmitting and sensing until a predefined portion of the object is radiated, wherein during each cycle, at least one of the first and second output signals are available to be processed; and
    processing the first and second output signals to provide an indication of the condition of the predefined portion of the object.

5. The method of claim 4 wherein the modifying of the beam of radiation comprises changing a frequency of the beam of radiation.

6. The method of claim 4 wherein the modifying of the beam of radiation comprises polarizing the beam of radiation.

7. A high-throughput inspection system comprising:
    an illumination system for sending a beam of radiation; and
    a controller for modifying the beam of radiation and enabling the illumination system to reflect the modified beam of radiation from a face of an area of an object so that the reflected beam alternately arrives at a first area sensor and a second area sensor,
    the first area sensor for sensing the reflected beam that arrives at the first area sensor and generating first output signals in response, and
    the second area sensor for sensing the reflected beam that arrives at the second area sensor and generating second output signals in response,
    wherein the controller is further adapted to; (i) control repeating of a cycle of modifying, reflecting and sensing until a predefined portion of the object is radiated; (ii) enable at least one of the first and second output signals to be processed during each cycle; and (iii) process the first and second output signals to provide an indication of a condition of the predefined portion of the object.

8. The system of claim 7 wherein the modifying of the beam of radiation comprises changing a frequency of the beam of radiation.

9. The method of claim 7 wherein the modifying of the beam of radiation comprises polarizing the beam of radiation.

10. A high-throughput inspection system comprising:
an illumination system for sending a beam of radiation; and
a controller for modifying the beam of radiation and enabling the illumination system to transmit the modified beam of radiation through a face of an area of an object so that the transmitted beam alternately arrives at a first area sensor and a second area sensor,
the first area sensor for sensing the transmitted beam that arrives at the first area sensor and generating first output signals in response and
the second area sensor for sensing the transmitted beam that arrives at the second area sensor and generating second output signals in response,
wherein the controller is further adapted to: (i) control repeating of a cycle of modifying, transmitting and sensing until a predefined portion of the object is radiated; (ii) enable, during each cycle, at least one of the first and second output signals to be processed; and (iii) process the first and second output signals to provide an indication of a condition of the predefined portion of the object.

11. The system of claim 10 wherein the modifying of the beam of radiation comprises changing a frequency of the beam of radiation.

12. The method of claim 10 wherein the modifying of the beam of radiation comprises polarizing the beam of radiation.

* * * * *